United States Patent
Marincek et al.

(10) Patent No.: US 9,186,222 B2
(45) Date of Patent: Nov. 17, 2015

(54) MANUALLY GUIDED ARTICULATED ARM

(75) Inventors: Marko Marincek, Ljubljana (SI); Jozica Kranjec, Lesce (SI); Matjaz Lukac, Ljubljana (SI)

(73) Assignee: Fotona d.d., Ljubljana (SI)

( * ) Notice: Subject to any disclaimer, the term of this patent is extended or adjusted under 35 U.S.C. 154(b) by 2206 days.

(21) Appl. No.: 12/203,567

(22) Filed: Sep. 3, 2008

(65) Prior Publication Data

US 2010/0057062 A1 Mar. 4, 2010

(51) Int. Cl.
*F16M 11/04* (2006.01)
*A61B 19/00* (2006.01)
*A61B 18/20* (2006.01)

(52) U.S. Cl.
CPC .............. *A61B 19/26* (2013.01); *A61B 18/201* (2013.01); *A61B 2019/263* (2013.01)

(58) Field of Classification Search
CPC ..... F16M 11/10; F16M 11/2021; F21V 21/26
USPC ......... 606/1; 74/589–595, 109, 469; 700/245; 749/589–595; 248/292.1; 901/48
See application file for complete search history.

(56) References Cited

U.S. PATENT DOCUMENTS

| | | | |
|---|---|---|---|
| 4,756,204 A * | 7/1988 | Wittwer et al. | 74/469 |
| 5,474,449 A | 12/1995 | Loge et al. | |
| 6,253,458 B1 | 7/2001 | Raab | |
| 6,564,667 B2 * | 5/2003 | Bayer et al. | 74/490.01 |
| 6,920,375 B2 * | 7/2005 | Enric | 700/258 |
| 2002/0165524 A1 * | 11/2002 | Sanchez et al. | 606/1 |
| 2004/0035243 A1 * | 2/2004 | Duval | 74/589 |
| 2004/0245419 A1 | 12/2004 | Sweere | |
| 2005/0252336 A1 | 11/2005 | Coral | |

FOREIGN PATENT DOCUMENTS

| | | |
|---|---|---|
| DE | 154282 A1 | 3/1982 |
| EP | 1632320 A | 3/2006 |
| WO | 2007054327 A | 5/2007 |

* cited by examiner

*Primary Examiner* — Aaron Roane
(74) *Attorney, Agent, or Firm* — Gudrun E. Huckett

(57) ABSTRACT

An articulated arm for applying a laser beam to a treatment zone has an arm section and a horizontal pivot joint. A spring arrangement acts on the pivot joint and has a cam disk and a pressure member following the cam disk contour as the arm section pivots. The arm section has, relative to a vertical direction, positive and negative pivot angle ranges. In the positive range the spring arrangement relieves the pivot joint from weight forces. When a resting angle in the negative range is reached the articulated arm rests in a support device. A total moment resulting from a weight force moment of the articulated arm and a restoring moment of the spring arrangement acts on the articulated arm about the pivot joint; cam disk contour and spring pretension are matched such that for the resting angle the total moment is oriented toward the support device.

16 Claims, 4 Drawing Sheets

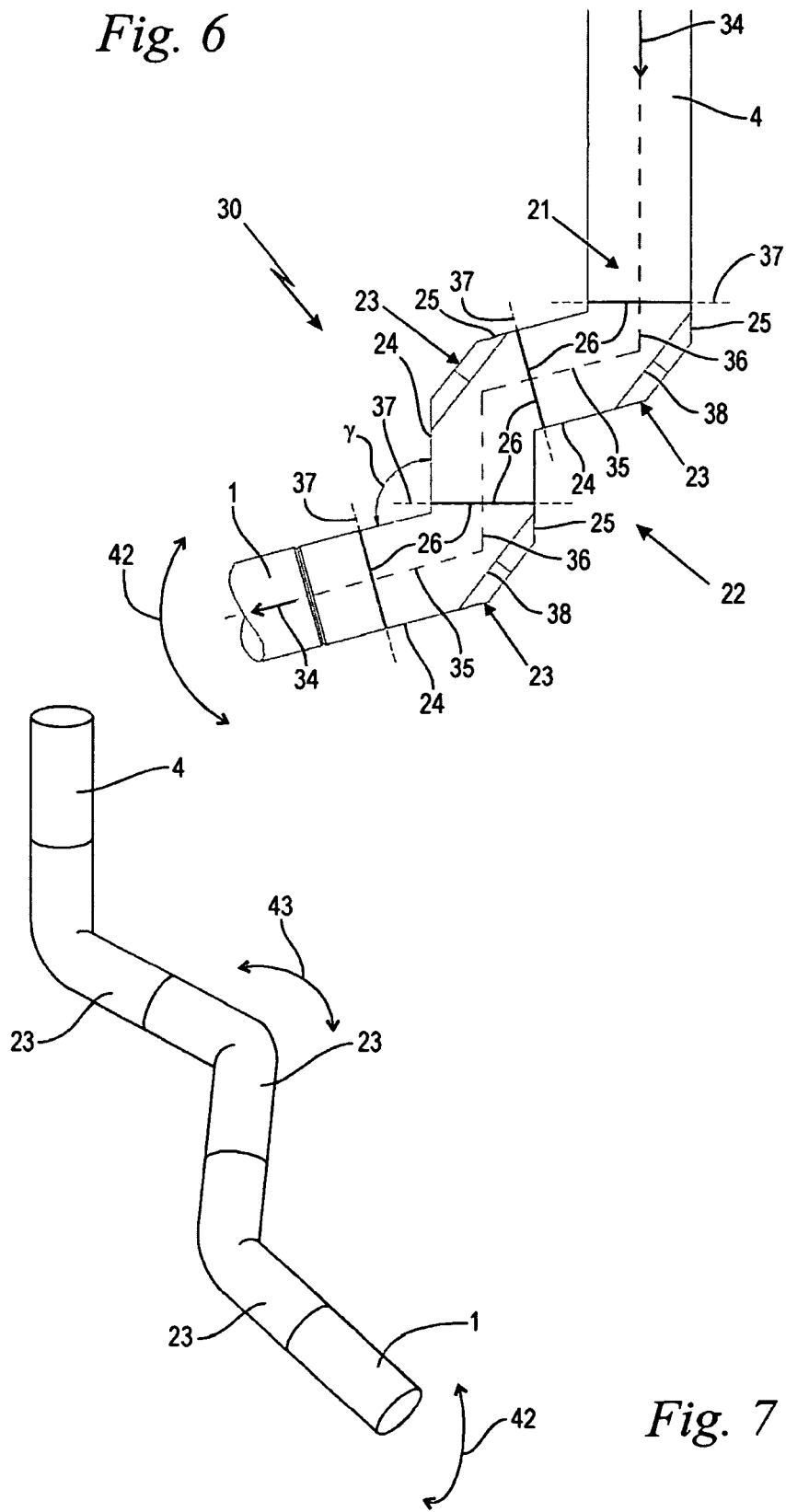

MANUALLY GUIDED ARTICULATED ARM

BACKGROUND OF THE INVENTION

The invention relates to a manually guided articulated arm that comprises a hand piece, in particular an optical hand piece for applying a laser beam to a treatment zone. The articulated arm has at least one arm section that is pivotably supported by means of a pivot joint about a pivot axis, wherein the pivot joint is provided with a spring arrangement acting about the correlated pivot axis.

Such an articulated arm is described in U.S. Pat. No. 5,474,449. The different arm sections of the articulated arm are pivotably connected to one another. The ends of the respective arm sections are angled by 90° and connected to intermediate torsion joints, respectively. An optical hand piece for applying a laser beam to a treatment zone, mounted on the outermost end of the articulated arm, is guided manually to the treatment zone wherein the articulated arm enables with its individual torsion joints a free movability of the hand piece in all six spatial degrees of freedom.

When using the aforementioned arrangement, a series of disadvantages is encountered. For a precise manual guiding action of the hand piece, it is necessary that its movement can be effected as effortless as possible. The weight of the articulated arm however is contrary to such a requirement and, without compensating measures, requires that an appropriate manual force be applied on the hand piece. U.S. Pat. No. 5,474,449 proposes different devices for relieving the weight. In one embodiment, a tension spring acts on a tension cable which is wound about a rotating disk in the first joint that is exposed to the greatest load. A moment resulting from the weight force in the correlated joint is at least partially compensated by the interaction of the tension spring with the disk. However, the tension spring has a linear spring characteristic and thus also a linear restoring characteristic. Moreover, by means of the illustrated tension cable only tension forces and no pressure forces can be transmitted. A weight-relieved pivoting action that goes beyond the vertical direction is therefore impossible.

Alternatively, U.S. Pat. No. 5,474,449 proposes a lever arm with a compensation weight. In order to generate a moment compensation, a correspondingly large lever arm or correspondingly large weight is required that restricts the movability of the articulated arm. Resting the articulated arm in a rest position and moving the articulated arm into a pivot range that is provided for operation are made more difficult.

In its resting position, the largest arm segment of both embodiments is arranged parallel to the axis of rotation of the compensated joint. During operation the aforementioned arm segment may be used within a larger angle range and even at 90° with respect to the axis of rotation of the compensated joint, applying a much larger weight force moment compared to the resting position. The operational weight force moment varies to a large and unpredictable extent. It is therefore hardly possible to generate within the entire pivot angle range a moment compensation for an effortless actuation.

Further disadvantages can be observed in the articulated arm section that immediately adjoins the hand piece. Three angle pieces are provided here that each have two arm segments positioned at a fixed angle of 90° relative to one another. At the ends of the short arm segments, a torsion joint is provided, respectively. Small, precise movements of the hand piece are enabled by the torsion joints of the three right-angle angle pieces without this requiring large spatial movements of the long arm sections that are farther located from the hand piece. For precise small spatial movements, a distinct easy movability of the torsion joints at the angle pieces is desired. However, it was found that when carrying out certain courses of movements, individual torsion joints have the tendency to jam or to make unpredictable flipping movements; this impairs the precision of the guiding action of the hand piece.

The invention has the object to further develop an articulated arm of the aforementioned kind such that a guiding action of the hand piece as effortless and precise as possible is enabled with simple means.

SUMMARY OF THE INVENTION

This object is solved by an articulated arm wherein the spring arrangement comprises a cam disk and a pressure member resting under spring pretension against the cam disk and guided along the contour of the cam disk as a function of a pivot angle of the arm section. The pivot joint has a substantially horizontal pivot axis that is positioned transversely to the weight force direction, wherein on the pivot joint with the horizontal pivot axis a positive pivot angle range of the arm section relative to a vertical direction is provided for operation, wherein in the positive pivot angle range the spring arrangement is provided for relieving the pivot joint from joint moments acting thereon and caused by weight forces, wherein on the pivot joint a negative pivot angle range of the arm section relative to the vertical direction with a resting angle is provided at which resting angle the articulated arm rests in a support device, and wherein the contour of the cam disk and the spring pretension of the pressure member are matched to one another such that for the resting angle a total moment, resulting from the weight force moment and a restoring moment and acting on the articulated arm about the pivot joint, is oriented in the direction toward the support device.

A manually guided articulated arm is proposed in which a spring arrangement provided on a pivot joint has a cam disk and a pressure member forced against the cam disk by spring pretension and guided along the contour of the cam disk as a function of a pivot angle of the arm section. The interaction of the pressure member and the cam disk generates a joint moment having a course that can be adjusted almost at will as a function of the pivot angle, respectively. For example, the circumferential contour of the cam disk can be shaped for generating a weight relief in such a way that at least approximately a sinus-shaped spring characteristic results. This counteracts in a compensating way the joint moment that is also sinus-shaped and is caused by the weight load. Onto such a sinus-shaped basic characteristic, an additional spring characteristic can be modulated by means of an appropriate curve design. This causes for example, in the case of a horizontal pivot axis, an automatic weight-relieved return of the articulated arm into a rest position outside of a working range of the pivot angle. From this rest position, the articulated arm can be guided against a minimal restoring force into the working range wherein the pivot angle can be guided to pass through the vertical direction. Within the working range of the pivot angle, the articulated arm can be moved almost without applying any manual forces.

The arrangement of cam disk and pressure member can be configured free of any redirections or other measures that impair precision. It is compact and precise wherein the free movability of the articulated arm is not impaired.

It can be expedient to mount the cam disk stationarily while the pressure member is connected to the pivotable arm section so as to commonly pivot with the arm section. However, in an advantageous further embodiment, the reverse configuration is selected in which the pressure member is stationary and, in particular, is secured on the stationary support and in which the cam disk is connected to the pivotable arm section so as to be entrained. The weight and size of the entrained parts are minimized so that a free movability of the articulated arm is enhanced.

The pressure member can be a glide shoe or the like and is advantageously configured as a roller that is moving on the contour of the cam disk and provided, in particular, with a ball bearing. The arrangement is precise and free of play. In particular, hysteresis effects are avoided. Each pivot angle is correlated with a precisely defined spring moment that is automatically adjusted independent of the selected pivot direction.

For example, the pressure member can be forced by means of a spring-tensioned swivel arm against the contour of the cam disk. In a preferred embodiment, a linear guide is provided for forcing the pressure member against the contour of the cam disk. Angular errors in the interaction with the cam disk are avoided. The desired course of moment is precisely reproducible.

For realizing the linear guide, two parallel guide rods are expediently provided on which a guide member supporting the pressure member is guided with linear slide bearings. Advantageously, for generating the spring pretension two coil pressure springs are preferably provided. In this way, with a simple configuration a precise canting-free guiding action and, as a result thereof, a reproducible course of the characteristic line of the spring arrangement is ensured.

According to an advantageous embodiment a manually operable device that can be actuated without requiring a tool is provided for adjusting the spring tension. Based on a spring tension that is set by the manufacturer, during operation the operator himself can carry out an adjustment that takes into consideration his personal habits and preferences, for example, in regard to a minimal residual weight force or in regard to a minimal restoring force that is present in the range of the operating angle. It is also possible to compensate differently acting weight forces when the hand piece is changed.

In a preferred embodiment, the pivotable arm section is supported by means of the pivot joint on a support wherein the pivot joint has a pivot axis that is substantially horizontal and extends transversely to the weight force direction. The support is preferably a stationary support. The spring arrangement is provided for relieving the pivot joint with regard to weight-induced joint moments. It is possible to adjust an at least approximately sinus-shaped course of the spring characteristic line that correspond essentially to the course of the weight force moment resulting from the articulated arm weight, that is approximately sinus-shaped as well. An almost angle-independent weight compensation across the entire pivot angle range that can extend on either side of the vertical direction is possible.

In an advantageous embodiment, at the pivot joint with the horizontal pivot axis a positive pivot angle range of the arm section relative to the vertical direction is provided for operation wherein the contour of the cam disk and the spring pretension of the pressure member are matched to one another within the positive pivot angle range such that a weight force moment deflecting the articulated arm and a restoring moment generated by the spring arrangement are in balance for a positive balance angle deviating from the vertical direction. This balance can be a labile or indifferent balance wherein in the range of the balance position a movement can be carried almost without applying any force. Advantageously, a stable balance position is provided. This enables the operator to let go of the hand piece at least for a short period of time. The articulated arm then assumes its balance position automatically and stays at rest in this position without automatically returning into the rest position or tilting to the ground.

In a further advantageous embodiment, a negative pivot angle range of the arm section that is negative relative to the vertical direction is provided and comprises a resting angle in which the articulated arm is resting in a support device. The contour of the cam disk and the spring pretension of the pressure member within the negative pivot angle range are matched to one another such that at the resting angle a total moment, resulting from the weight force moment and the restoring moment acting on the articulated arm about the pivot joint, acts in the direction of the support device. As a result of the acting total moment the articulated arm is positioned safely in the support device. The acting restoring moment of the spring arrangement compensates however the weight force moment only to a certain degree so that the articulated arm at the time of initiating operation can be pivoted out of the support device into the operating position with minimal force.

Expediently, the total moment is oriented within the entire negative pivot angle range, in particular, including the vertical direction, in the direction toward the support device. After completion of operation, the articulated arm must not be returned completely into the rest position; instead, it is sufficient to move the articulated arm into the vicinity of the vertical direction. When in such a position, a total moment will act that pivots the articulated arm automatically into the support device; this improves ease of operation.

In another advantageous embodiment, the articulated arm comprises in addition to the first arm section with the weight-relieved pivot joint a second arm section that is supported by means of a second pivot joint at a free end of the first arm section. The hand piece is arranged in the area of a free end of the second arm section. The arrangement enables an almost unrestricted spatial movability of the hand piece. The total center of gravity of the articulated arm changes with the pivot angle of the second arm section without this having an effect on the restoring moment of the spring arrangement of the first arm section. However, an appropriate adjustment of the spring arrangement can be made such that across the entire pivot angle range of the second arm section the occurring weight force moment is compensated at least approximately so that the manual forces become minimal. In the rest position, the second arm section can be placed parallel against the first arm section. In this way, a minimal stowing space is required.

Preferably, the first arm section and, in particular, the entire articulated arm, is pivotably supported by means of a pivot joint about an essentially vertical pivot axis that is arranged approximately parallel to the weight force, wherein the correlated spring arrangement is provided for restoring the pivot joint from a deflected position into a neutral position. After usage, the articulated arm automatically assumes its neutral position from where it can be easily returned into its rest position in which it can be deposited in a corresponding support device.

In a preferred embodiment, the articulated arm has, in immediate vicinity of the hand piece, particularly between the free end of the second arm section and the hand piece, an articulated arm section with at least two, preferably three, angle pieces that are each provided with two arm segments positioned at a fixed angle relative to one another. At the ends of the arm segments a torsion joint of the articulated arm is provided, respectively, wherein the angle of the arm segments relative to one another differs from 90°. In particular, the angle is greater than 100° and is especially preferred approximately 105°. It was surprisingly found that the jamming of the torsion joints that is observed in the prior art at angles of 90°, no longer occurs when angles are selected in accordance with the invention. The residual friction moments and break-away moments in the torsion joint are reliably overcome. In the case of a free small-size movement of the hand piece, all torsion joints stay in motion so that a precise working or precise guiding of the hand piece is simplified.

BRIEF DESCRIPTION OF THE DRAWINGS

One embodiment of the invention will be explained in the following in more detail with the aid of the drawings.

FIG. 6 is an enlarged detail view of the articulated arm according to FIG. 1 in the area of its multi-articulated arm section adjoining the hand piece and comprised of three angle pieces.

FIG. 7 is a schematic perspective view of the articulated arm section according to FIG. 6 illustrating the relative movement of individual angle pieces as a result of a movement of the hand piece.

DESCRIPTION OF PREFERRED EMBODIMENTS

Figures 1, 2:
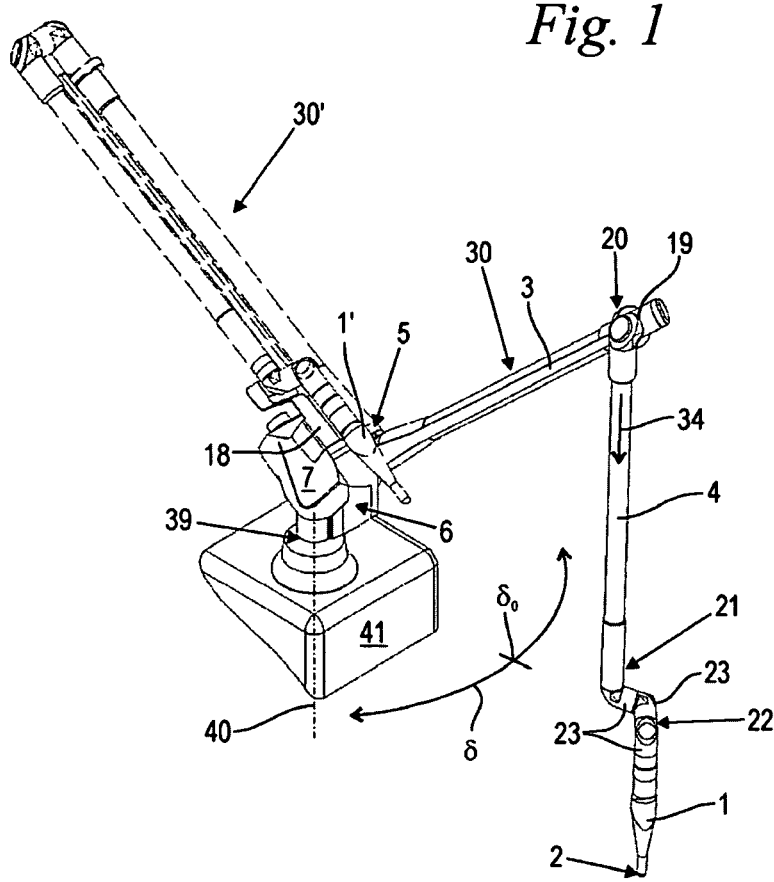
FIG. 1 is a perspective illustration of a manually guided articulated arm according to the invention with an optical hand piece.
FIG. 2 shows a side view of the articulated arm according to FIG. 1 with details in regard to the acting weight forces and the resulting moments for different pivot angles for the operating and rest positions.

FIG. 1 shows in a perspective view a manually guided articulated arm 30 embodied in accordance with the invention. The articulated arm 30 comprises a stationary support 6 that is pivotable by means of a pivot joint 39 about a vertical pivot axis 40; a first arm section 3 and a second arm section 4; an articulated arm section 22; and a hand piece 1. The first arm section 3 is supported by means of a pivot joint 5 with a horizontal pivot axis 29 (FIG. 2, 3) on the stationary support 6. On the free end 20 of the first arm section 3 positioned opposite the pivot joint 5, an additional pivot joint 19 is provided with which the second arm section 4 is pivotably supported on the first arm section 3. In the area of the free end 21 of the second arm section 4, the hand piece 1 is arranged. Between the free end 21 of the second arm section 4 and the hand piece 1, the articulated arm section 22 is arranged that comprises at least two, in the illustrated embodiment three, angle pieces 23. The angle pieces 23 will be explained in more detail in connection with FIGS. 6 and 7.

The articulated arm 30 is provided for manually guiding a medical treatment device. In the illustrated embodiment, an optical hand piece 1 with a laser optic 2, not illustrated in detail, is provided for medical treatment. By means of the laser optic 2, an externally generated laser beam, illustrated by arrow 34, is guided by angled mirrors through the articulated arm 30 to the treatment location. Instead of the optical hand piece 1 it is also possible to provide other medical treatment devices, for example, an ultrasound head, a dental drill or similar devices. Non-medical devices may be provided as well.

The articulated arm, referenced by reference numeral 30 and shown in solid lines, is illustrated in an angular position that is provided for operation. In this connection, the weight force of the articulated arm 30 causes a pivot moment about the pivot joint 5 on the support 6; for compensating the weight, a spring arrangement 7 is provided which will be explained in connection with FIGS. 3 to 5 in more detail.

By pivot movements of the pivot joints 5, 19, the articulated arm 30 can be pivoted back and forth between its operating position and a rest position in which the articulated arm is identified by reference numeral 30'. In its rest position, the articulated arm 30' rests with its hand piece 1' in the indicated support device 18.

The articulated arm 30 can also be manually pivoted as a whole about the vertical pivot axis 40 about swivel angle $\delta$. The pivot axis 40 is positioned at least approximately parallel to the weight force direction so that moments caused by the weight force on the pivot joint 39 about the pivot axis 40 are of subordinate importance. Relative to the swivel angle $\delta$ positioned in the horizontal plane, a neutral position of the articulated arm 30 is indicated by neutral angle $\delta_0$ within which the articulated arm 30 can be moved from its illustrated operating position into the rest position indicated by 30' and placed onto the support device 18. Starting from the neutral angle $\delta_0$, the articulated arm 30 can be swiveled or deflected in the operating position about the pivot angle $\delta$ in both directions. The correlated pivot joint 39 with vertical pivot axis 40 is provided optionally with a spring arrangement 41, not illustrated in detail and explained infra. By means of a restoring moment, the spring arrangement 41 can move the articulated arm 30 automatically from a position deflected in any direction about pivot angle $\delta$ into the neutral angle position 60. Based thereon, a manual swivel action about the angle $\delta$ is carried out against the restoring moment of the spring arrangement 41. The automatic restoring action into the neutral angle $\delta_0$ enables a simplified transition into the rest position 30'.

FIG. 2 shows the arrangement according to FIG. 1 in a side view. As a reference point for angle values for a pivoting action of the first arm section 3, a vertical direction 17 has been selected that extends through a pivot axis 29 of the pivot joint 5 positioned between the first arm section 3 and the stationary support 6. The pivot axis 29 is horizontal and thus at a right angle to the vertical direction 17 or to the weight force direction.

For the operation of the articulated arm 30, a positive pivot angle range +$\alpha$ of the arm section 3 is provided relative to the vertical direction 17. The articulated arm 30 is shown within the positive pivot angle range +$\alpha$ at a balance angle $\alpha_1$ to be described infra in connection with FIG. 4. In the same pivot plane the second arm section 4 is pivotable relative to the first arm section 3 at the pivot joint 19 about the angle $\beta$. The pivot axis of the pivot joint 19 is also horizontal and parallel to the pivot axis 29. In the illustrated balance position, the hand piece 1 has been released by the operator so that the arm section 4 with the hand piece 1 is freely suspended under the action of the weight force. Based on this position, by manually guiding the hand piece 1 the pivot angle $\beta$ can be enlarged or decreased. Moreover, a greater or smaller pivot angle $\alpha$ relative to the balance angle $\alpha_1$ can be adjusted.

The movable part of the articulated arm 30 has a center of gravity 27 in which a weight force 28 acts parallel to the vertical direction 17. At the balance angle $\alpha_1$ the weight force 28 relative to the pivot axis 29 of the pivot joint 5 has a distance vector from the pivot axis 29 to the center of gravity 27, the horizontal projection of the distance vector defining a lever arm $R_1$. The cross product of weight force 28 and lever arm $R_1$ results in a weight force moment $Mg_1$, its vector being disposed parallel to the pivot axis 29. The weight force moment $Mg_1$ acts in the clockwise direction on the first arm section 30, and tends to increase the absolute value of the pivot angle $\alpha$. The course of the weight force moment $Mg_1$ as a function of the pivot angle $\alpha$ is essentially sinus-shaped.

From its operating position, the movable part of the articulated arm 30 can be pivoted through the vertical direction 17 into a negative angle range $-\alpha$. Within the negative angle range $-\alpha$, a resting angle $\alpha_2$ is provided in which the articulated arm 30' rests in the support device 18 (FIG. 1). At the center of gravity 27' of the articulated arm 30', a weight force 28' acts with a lever arm $R_2$ about the pivot axis 29 of the pivot joint 5. This leads to a weight force moment $Mg_2$ acting counterclockwise in the direction of the resting angle $\alpha_2$, analog to the weight force moment $Mg_1$ at a positive pivot angle $\alpha$.

Figure 3:
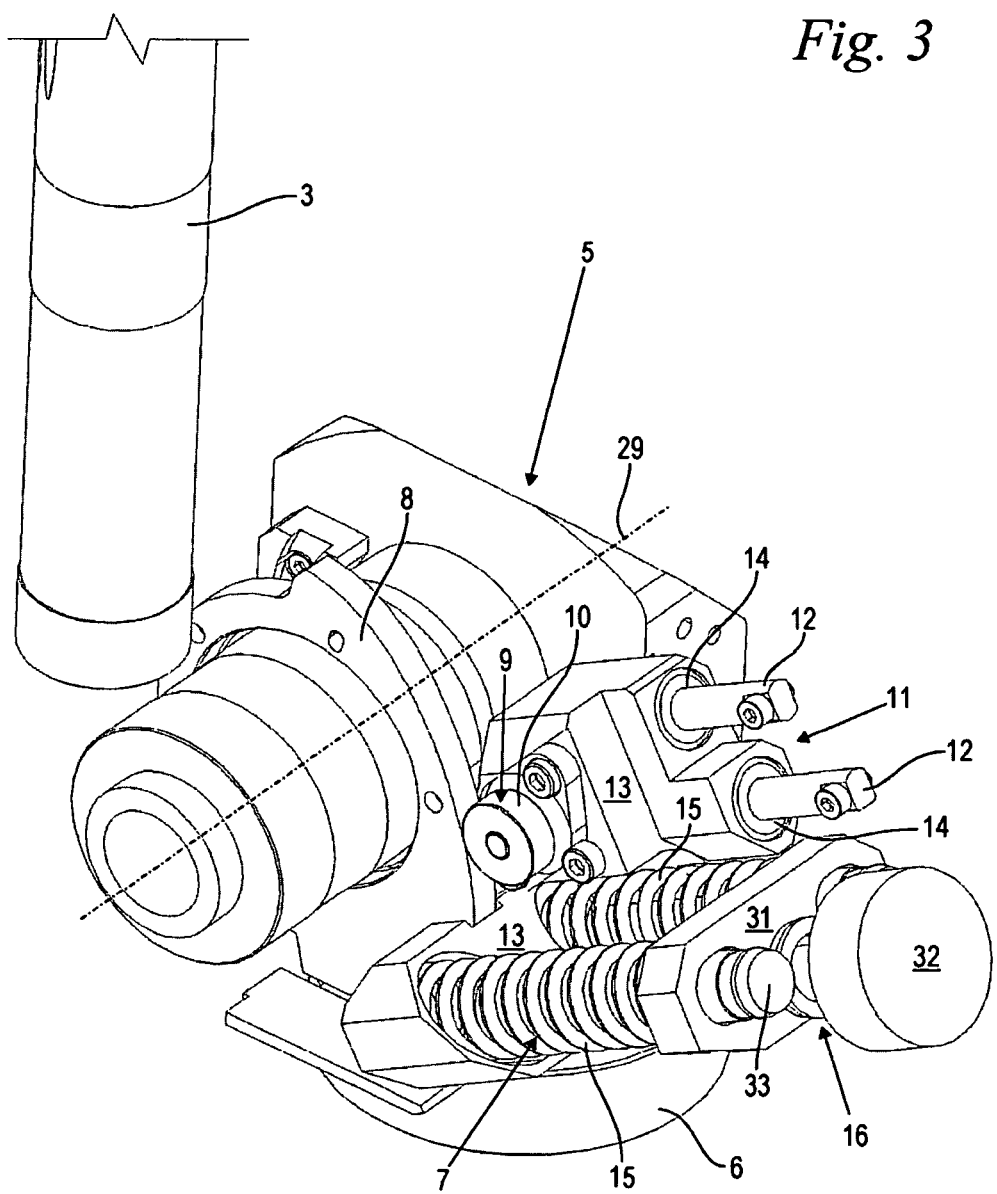
FIG. 3 shows a perspective detail view of the spring arrangement of the pivot joint according to FIGS. 1 and 2 with details of the arrangement of a cam disk and a pressure member rolling thereon.

For influencing the moment acting on the pivot joint 5 and in particular for providing relief from the weight force moments $Mg_1$, $Mg_2$, the spring arrangement 7 is provided that is schematically indicated in FIG. 1 and illustrated in detail in the perspective view of FIG. 3. The spring arrangement 7 has a cam disk 8 and a pressure member 9 that rests against the circumferential contour of the cam disk 8 under spring pretension and is guided along the contour of the cam disk 8 as a function of the pivot angle $\alpha$ of the arm section 3 (FIG. 2). The cam disk 8 is connected to the pivotable arm section 3 so as to be entrained by it. The pressure member 9 is secured by means of a linear guide 11 on the stationary support 6.

The pressure member 9 can be a glide shoe or a similar device and is configured in the illustrated embodiment as a ball bearing-supported roller 10 that rolls on the circumferential contour of the cam disk 8. A pair of coil pressure springs 15 is part of the spring arrangement 7; the springs 15 force with elastic pretension the pressure member 9 against the circumferential contour of the cam disk 8. Instead of the coil pressure springs 15 it is also possible to employ a leg spring or the like that forces the pressure member 9 by means of a pivot arm against the cam disk 8. In the illustrated embodiment, the coil pressure springs 15 act on the linear guide 11 by means of which the pressure member 9 is forced by a straight, linear movement against the cam disk 8.

The linear guide 11 comprises two parallel guide rods 12 on which a guide member 13 supporting the pressure member 9 is guided with two linear slide bearings 14. The longitudinal axes of the guide rods 12 are positioned approximately radially to the pivot axis 29 of the pivot joint 5 so that the guide member 13 together with the pressure member 9 is forced radially inwardly toward the pivot axis 29 against the outer circumferential contour of the cam disk 8 from the exterior. Alternatively, a reverse configuration can be expedient in which the cam disk 8 has an opening with an inner curved contour wherein the pressure member 9 is forced radially from the interior outwardly against this inner contour in the radial direction.

A further part of the spring arrangement 7 is comprised of a manually operated device 16 that requires no tools for actuation and enables adjustment of the spring pretension. For this purpose, two parallel guides 33 are provided that pass through the two coil pressure springs 15; a pressure plate 31 is axially movably guided on the guides 33. The manually actuatable knurled screw 32, requiring no tool, is provided for axial movement of the pressure plate 31 relative to the support 6 so that the spring pretension of the coil pressure springs 15 arranged therebetween can be adjusted or matched. The longitudinal axes of the coil pressure springs 15 and of the guides 33 are positioned axis-parallel to the two guide rods 12.

Figure 4:
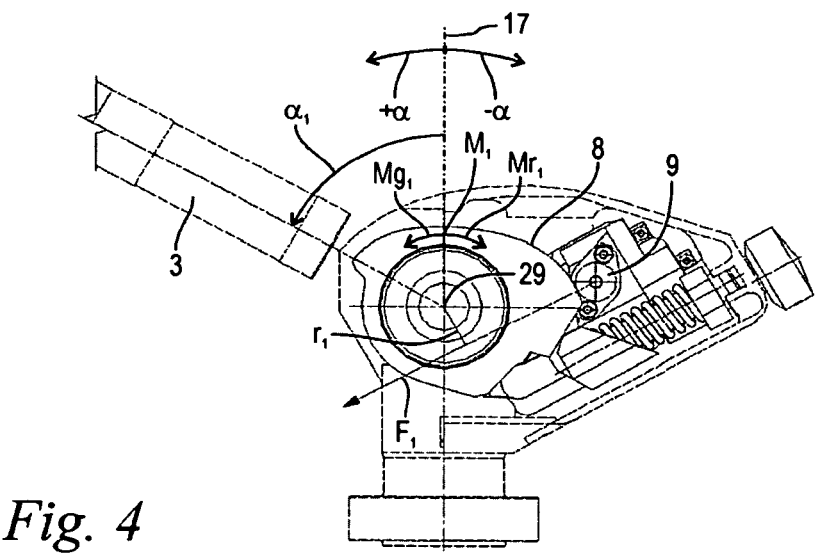
FIG. 4 shows a side view of the arrangement according to FIG. 3 with articulated arm pivoted into the operating position for illustrating the restoring moment generated by the spring arrangement.

FIG. 4 shows a side view of the arrangement according to FIG. 3 with the arm section 3 at the balance angle $\alpha_1$. By looking also at FIG. 2, wherein the same features are identified with same reference numerals, it is apparent that at the balance angle $\alpha_1$ the weight force moment $Mg_1$ is acting in the direction of the positive pivot angle range $+\alpha$.

The circumferential contour of the cam disk 8 and the spring pretension of the pressure member 9 adjusted in accordance with FIG. 3 are matched to one another in such a way that the pressure member 9 with its force $F_1$ acts with a lever arm $r_1$ relative to the pivot axis 29 on the circumferential contour of the cam disk 8. The lever arm $r_1$ is the projection of the distance vector between the pivot axis 29 and the contact point of the pressure member 9 and the cam disk 8 onto a plane that is perpendicular to the force $F_1$ and includes the pivot axis 29. The force $F_1$ and the lever arm $r_1$ generate a restoring moment $Mr_1$, whose vector being disposed parallel to the pivot axis 29. The restoring moment $Mr_1$ counteracts the weight force moment $Mg_1$ and acts on the first arm section 30 toward the vertical direction 17. For the balance angle $\alpha_1$, the absolute value of both moments is identical but oppositely oriented. They are in balance so that a resulting moment $M_1$ acting about pivot axis 29 is generated that has the absolute value zero. The balance between the weight force moment $Mg_1$ and the restoring moment $Mr_1$ is a stable balance so that the articulated arm 30 at the balance angle $\alpha_1$ according to FIG. 2 maintains its position automatically even when the hand piece 1 (FIG. 2) is let go of.

Figure 5:
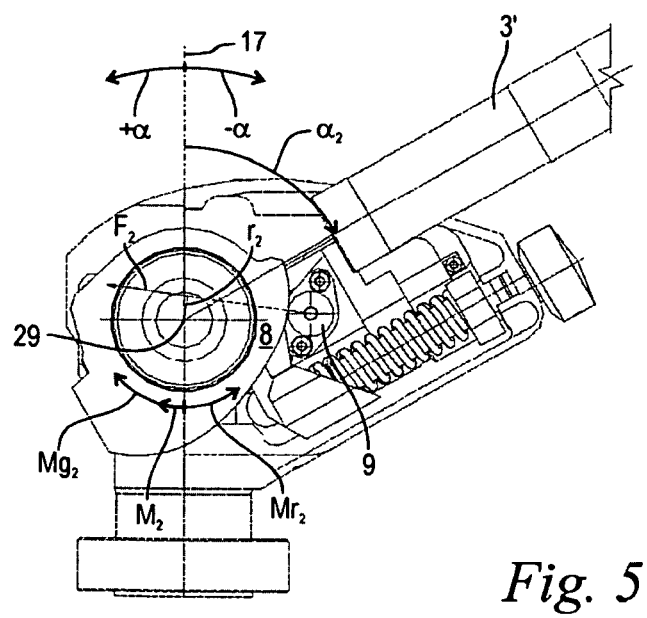
FIG. 5 shows the arrangement according to FIG. 4 with the articulated arm in the rest position.

FIG. 5 shows the arrangement according to FIG. 4 with the first arm section 3' at the rest angle $\alpha_2$ wherein the weight force moment $Mg_2$ according to FIG. 2 acts clockwise in the direction of the negative pivot angle range $-\alpha$, i.e., has the tendency to enlarge the absolute value of the resting angle $\alpha_2$. The contour of the cam disk 8 and the spring pretension of the pressure member 9 are adjusted relative to one another such that at the resting angle $\alpha_2$ the pressure member 9 acts with pressure force $F_2$ against the circumferential contour of the cam disk 8; the pressure force $F_2$ has a lever arm $r_2$ relative to the pivot axis 29. Pressure force $F_2$, lever arm $r_2$ and a resulting restoring moment $Mr_2$ are defined analog to pressure force $F_1$, lever arm $r_1$ and restoring moment $Mr_1$.

At the resting angle $\alpha_2$ the pressure force $F_2$ generates together with the corresponding lever arm $r_2$ a counterclockwise acting restoring moment $Mr_2$ in the direction toward the positive pivot angle range $+\alpha$ and thus opposite to the weight force moment $Mg_2$. The restoring moment $Mr_2$ has a smaller absolute value in comparison to the weight force moment $Mg_2$ so that the resulting total moment $M_2$ acting on the arm section 3' acts in the clockwise direction, i.e., has the tendency to enlarge the resting angle $\alpha_2$ of the arm section 3'. In this way, the arm section 3' or the entire movable part of the articulated arm 30' is forced into the support device 18 (FIG. 1). The restoring moment $Mr_2$ acts however as a relief so that only minimal forces or moments must be applied by hand in order to lift the articulated arm 30' from the position defined by resting angle $\alpha_2$ and to move it into the operating position 30 according to FIG. 4.

When looking at both FIG. 4 and FIG. 5, it can be seen that the pressure forces $F_1$ and $F_2$ starting at the pressure member 9 have different orientations and pass on different sides of the pivot axis 29, i.e., generate moments $Mr_1$, $Mr_2$ with different sign. This is a result from the course of the circumferential contour of the cam disk 8. The configuration of the pressure member 9 as an almost friction-free roller allows only forces in the direction of the surface normal of the cam disk 8 but no tangential forces. This holds true for the entire pivot angle range $-\alpha$, $+\alpha$. By means of constructive configuration of the circumferential contour of the cam disk, a course of the surface normal results that depends on the pivot angle $\alpha_1$ this course presets the course of the direction of the pressure forces $F_1$ and $F_2$ depending on the pivot angle $\alpha$. The local radius of the circumferential contour of the cam disk 8 is moreover a measure for the linear deflection of the pressure member 9 and thus also for the pretension of the coil pressure springs 15 (FIG. 3) and, as a result thereof, for the absolute value of the pressure forces $F_1$ and $F_2$. In this way, restoring moments $Mr_1$, $Mr_2$ with any sign and any absolute value, including the absolute value zero, can be adjusted.

From the description of FIG. 2 it can be taken that the weight force moment Mg is approximately zero when the articulated arm 30 is positioned perpendicularly to the vertical direction 17. The contour of the cam disk 8 and the pressure force of the pressure member 9 are adjusted relative to one another such that in this position a restoring moment Mr corresponding to the restoring moment $Mr_1$ according to FIG. 4 results. In connection with the missing weight force moment Mg a small resulting moment M is generated in accordance with the resulting moment $M_2$ according to FIG. 5. In this connection, the adjustment of the spring arrangement 7 (FIG. 3) is selected such that the total moment $M_2$ within the entire negative pivot angle range $-\alpha$, including the vertical direction 17, is oriented in the direction toward the support device 18 (FIG. 1). In particular, in this angle range the total moment $M_2$ in accordance with illustration of FIG. 5 is of a small, approximately constant absolute value.

The spring arrangement 41 acting about the vertical pivot axis 40 of the pivot joint 39 and illustrated in FIG. 1 is configured according to the same principle as the spring arrangement 7 according to FIGS. 1 and 3 to 5. The contour of a corresponding cam disk 8 and the spring pretension of a corresponding pressure member 9 are adjusted relative to one another such that the return of the articulated arm 30 into the neutral angle $\delta_0$ is initiated as described in connection with FIG. 1.

Another option in connection with or as an alternative to the described spring arrangement 7 to compensate the weight as a function of pivot angle could be the use of a servo motor. The pivot angle would be detected by suitable means and the driving current would be numerically determined to produce a corresponding moment by the servo motor for the desired weight relief.

FIG. 6 shows an enlarged side view of the articulated arm 30 in the area of its articulated arm section 22 arranged between the second arm section 4 and the hand piece 1. Three angle pieces 23 are provided that each have two arm segments 24, 25 positioned at a fixed angle γ relative to one another. The three angle pieces 23 are configured to be identical wherein a long arm segment 24 of a first angle piece 23 adjoins a short arm segment 25 of the neighboring angle piece 23. The free end 21 of the second arm section 4 adjoins a short arm segment 25 of the neighboring angle piece 23 while the hand piece 1 adjoins a long arm segment 24 of the neighboring angle piece 23. Segment axes 35, 36 of the arm segments 24, 25 are positioned at a fixed unchangeable angle γ relative to one another; the angle γ differs from 90° and is preferably greater than 100°; in particular, it is approximately 105° in the illustrated embodiment.

In the corner areas of each angle piece 23 a mirror 38 is provided that is positioned perpendicularly to the bisecting line of the angle γ. In this way, the laser beam that is introduced parallel to the longitudinal axis of the second arm section 4 in accordance with arrow 34 is guided through the angle pieces 23 parallel to the segment axes 35, 36 and parallel to the longitudinal axis of the hand piece 1.

At the ends of each arm segments 24, 25 a torsion joint 26 of the articulated arm 30 is provided and forms a joint plane 37, respectively. The hand piece 1, the second arm section 4, and all three angle pieces 23 are rotatable relative to one another in the joint planes 37 about their respective longitudinal axes or segment axes 35, 36 in a torsion movement. By means of a manual movement of the hand piece 1 in all six spatial degrees of freedom, torsion moments result in the individual joint planes 37, the torsion vectors being parallel to the segment axes 35, 36, and causing an articulated movement about the respective segment axes 35, 36.

However, under certain conditions a free movement of the hand piece 1 is limited. In the case of FIG. 6 for example, when all three angle pieces 23 are disposed in one common plane, a swiveling movement of the end piece 1 within this plane as indicated by arrow 42 is impossible. A displacement of the angle pieces 23 slightly out of the common plane is necessary. In practical use, at least a minimal out-of-plane displacement is essentially present all the time, as depicted in FIG. 7. Upon a swiveling movement of hand piece 1 according to arrow 42 in FIG. 7, the out-of-plane displacement of individual angle pieces 23 is increased or decreased, as indicated for example by an arrow 43 for the middle angle piece 23.

In connection with state of the art 90° angle pieces it was found, that small movements of the hand piece 1 according to arrow 42 result in comparatively large movements of one or more angle pieces 23 according to arrow 43. Under certain circumstances a sudden flipping movement of single angle pieces 23 up to an angle of about 90° is encountered, which severely impares the precision of the guiding action of the hand piece 1.

It has been surprisingly found that a movement of a hand piece 1 connected to angle pieces 23 with an angle γ as described along with FIG. 6, results in much smoother and significantly smaller movements of the angle pieces 23. Smaller hand forces are required at the hand piece 1 to generate these movements. The smaller hand forces in connection with the smoother and smaller movements of the angle pieces 23 lead to a significantly higher precision, when manually guiding the hand piece 1 to the treatment zone.

While specific embodiments of the invention have been shown and described in detail to illustrate the inventive principles, it will be understood that the invention may be embodied otherwise without departing from such principles.

What is claimed is:

1. A manually actuated articulated arm comprising:
   an optical hand piece for applying a laser beam to a treatment zone;
   a first arm section;
   a first pivot joint connected to the first arm section such that the first arm section is pivotably supported by the first pivot joint for pivoting about a horizontal pivot axis;
   a spring arrangement acting on the first pivot joint about the pivot axis, wherein the spring arrangement comprises a cam disk and a pressure member that rests under spring pretension against the cam disk and is guided along a contour of the cam disk as a function of a pivot angle of the first arm section;
   wherein the horizontal pivot axis is positioned transversely to a weight force direction of a weight force of the articulated arm;

wherein the first arm section has, relative to a vertical direction, a positive pivot angle range and a negative angle range about the pivot axis;

wherein the first arm section has a working angle range only within the positive pivot angle range and wherein the contour of the cam disk imparts to the spring arrangement a spring characteristic that is asymmetric relative to the vertical direction so that the spring characteristic in the positive pivot angle range is different from the spring characteristic in the negative pivot angle ranges;

wherein, within the positive angle range, the spring characteristic is adjusted such that, in the working angle range, the spring arrangement almost angle-independently relieves the first pivot joint from joint moments, caused by weight forces of the articulated arm and acting on the first pivot joint, and movement of the articulated arm is enabled almost without applying any manual force;

wherein a resting angle of the first arm section is provided within the negative angle range, wherein when the resting angle is reached the articulated arm rests in a support device;

wherein a total moment resulting from a weight force moment of the articulated arm and a restoring moment of the spring arrangement is acting on the articulated arm about the first pivot joint; and wherein the contour of the cam disk and the spring pretension of the pressure member are matched to one another such that for the resting angle the total moment is oriented in a direction toward the support device.

2. The articulated arm according to claim 1, wherein the pressure member is stationarily secured and the cam disk is connected to the first arm section so as to be entrained by the first arm section.

3. The articulated arm according to claim 1, wherein the pressure member is embodied as a roller rolling on the contour of the cam disk.

4. The articulated arm according to claim 3, wherein the pressure member is provided with a ball bearing.

5. The articulated arm according to claim 1, comprising a linear guide forcing the pressure member against the contour of the cam disk.

6. The articulated arm according to claim 5, wherein the linear guide comprises two parallel guide rods and a guide member guided with slide bearings on the guide rods, wherein the guide member is connected to the pressure member and supports the pressure member.

7. The articulated arm according to claim 1, wherein the spring arrangement comprises at least one coil pressure spring for generating the spring pretension.

8. The articulated arm according to claim 7, wherein for generating the spring pretension two of said at least one coil pressure spring are provided.

9. The articulated arm according to claim 1, comprising a manually operable device for adjusting the spring pretension wherein the manually operable device requires no tool for actuation.

10. The articulated arm according to claim 1, comprising a support wherein the first pivot joint is mounted on the support and the first arm section is supported by the first pivot joint on the support.

11. The articulated arm according to claim 10, wherein the support is stationary.

12. The articulated arm according to claim 1, wherein the contour of the cam disk and the spring pretension of the pressure member are matched to one another such that in the positive angle range a positive balance angle is provided where the weight force moment deflecting the articulated arm and the restoring moment generated by the spring arrangement are in balance.

13. The articulated arm according to claim 12, wherein the balance between the weight force moment and the restoring moment is a stable balance.

14. The articulated arm according to claim 1, wherein the total moment within the entire negative pivot angle range is oriented in a direction toward the support device.

15. The articulated arm according to claim 14, wherein the total moment for the first arm section in the vertical direction is oriented in the direction toward the support device.

16. The articulated arm according to claim 1, further comprising a second arm section and a second pivot joint wherein the second pivot joint is connected to a free end of the first arm section and the second arm section is connected to the second pivot joint so as to be pivotable about the second pivot joint, wherein the hand piece is arranged at a free end of the second arm section.

* * * * *